United States Patent
Lee et al.

(10) Patent No.: US 10,510,448 B2
(45) Date of Patent: Dec. 17, 2019

(54) METHOD FOR PROVIDING DIAGNOSIS AID INFORMATION BY USING MEDICAL IMAGES, AND SYSTEM THEREFOR

(71) Applicant: SAMSUNG LIFE PUBLIC WELFARE FOUNDATION, Seoul (KR)

(72) Inventors: Won Jae Lee, Seoul (KR); Jae Hun Kim, Seoul (KR)

(73) Assignee: Samsung Life Public Welfare Foundation (KR)

( * ) Notice: Subject to any disclaimer, the term of this patent is extended or adjusted under 35 U.S.C. 154(b) by 329 days.

(21) Appl. No.: 15/527,114

(22) PCT Filed: Nov. 17, 2015

(86) PCT No.: PCT/KR2015/012354
§ 371 (c)(1),
(2) Date: May 16, 2017

(87) PCT Pub. No.: WO2016/080736
PCT Pub. Date: May 26, 2016

(65) Prior Publication Data
US 2019/0214133 A1      Jul. 11, 2019

(30) Foreign Application Priority Data

Nov. 17, 2014  (KR) .................. 10-2014-0160135

(51) Int. Cl.
*G06K 9/00* (2006.01)
*G16H 50/20* (2018.01)
(Continued)

(52) U.S. Cl.
CPC ............. *G16H 50/20* (2018.01); *G16H 30/40* (2018.01); *A61B 6/03* (2013.01); *G06Q 50/10* (2013.01); *G06T 7/0012* (2013.01)

(58) Field of Classification Search
None
See application file for complete search history.

(56) References Cited

U.S. PATENT DOCUMENTS

2009/0122953 A1* 5/2009 Imai ................ A61B 6/032
378/5
2009/0207967 A1  8/2009 Liu et al.
(Continued)

FOREIGN PATENT DOCUMENTS

JP       2008-86543 A    4/2008
JP       2008086543      4/2008
(Continued)

OTHER PUBLICATIONS

Wang, Zhijun, et al. "Three-dimensional evaluation of lipiodol retention in HCC after chemoembolization: a quantitative comparison between CBCT and MDCT." Academic radiology21.3 (2014): 393-399. (Year: 2014).*

(Continued)

*Primary Examiner* — Sean M Conner
(74) *Attorney, Agent, or Firm* — Myers Bigel, P.A.

(57) ABSTRACT

The present invention relates to a method and system for providing 'diagnosis-aiding information', the method and system being capable of diagnosing cancer and the like of a patient by using medical imaging. According to the present invention, the system for providing the diagnosis-aiding information comprises: the image receiving part for receiving the medical images acquired in the first energy band and the medical images acquired in the second energy band; and the 'analysis- and diagnosis-aiding information providing part for providing diagnosis-aiding information generated by analyzing the medical image acquired in the first energy band and the medical image acquired in the second energy band, wherein the 'analysis and diagnosis-aid information providing unit' provides the diagnosis-aiding information by (Continued)

measuring the HU values in the region of interest (ROI) of the medical images acquired in the first energy band and the medical images acquired in the second energy band and comparing the HU values of the ROI of two medical images.

18 Claims, 7 Drawing Sheets

(51) Int. Cl.
    *G16H 30/40*     (2018.01)
    *A61B 6/03*     (2006.01)
    *G06Q 50/10*     (2012.01)
    *G06T 7/00*     (2017.01)

(56) References Cited

U.S. PATENT DOCUMENTS

2010/0278407 A1    11/2010    Dzyubak et al.
2012/0250967 A1*  10/2012    Flohr ..................... A61B 6/12
                                                        382/131

FOREIGN PATENT DOCUMENTS

| KR | 10-2011-0009522 A | 1/2011 |
| KR | 1020110009522 | 1/2011 |
| KR | 10-2014-0118539 A | 10/2014 |
| KR | 1020140118539 | 10/2014 |

OTHER PUBLICATIONS

Written Opinion and International Search Report Corresponding to International Patent Application No. PCT/KR2015/012354 dated Nov. 17, 2015 (37 pages).

International Search Report, Application No. PCT/KR2015/012354, dated Feb. 26, 2016.

Written Opinion of the International Searching Authority, Application No. PCT/KR2015/012354, dated Feb. 26, 2016.

* cited by examiner

METHOD FOR PROVIDING DIAGNOSIS AID INFORMATION BY USING MEDICAL IMAGES, AND SYSTEM THEREFOR

CROSS REFERENCE TO RELATED APPLICATIONS

This application is a 35 U.S.C. § 371 national stage application of PCT International Application No. PCT/KR2015/012354, filed on Nov. 17, 2015, which itself claims the benefit of Korean Patent Application No. 10-2014-0160135, filed Nov. 17, 2014, the disclosure and content of both of which are incorporated by reference herein in their entireties. The above-referenced PCT International Application was published in the Korean language as International Publication No. WO 2016/080736 A1 on May 26, 2016.

TECHNICAL FIELD

The present invention relates to a method and system for providing 'diagnosis-aiding information', the method and system being capable of providing subsidiary information in diagnosing cancer and the like of a patient, by using medical imaging, and more particularly, to a method and system for providing diagnosis-aiding information by using medical imaging acquired in a plurality of energy bands. According to the present invention, it is possible to initially diagnose a cancer and also easily differentiate a residual/recurrent tumor from a necrotic tumor after treatment.

BACKGROUND ART

Typically, liver tissue receives oxygen and nourishment through two types of blood vessels: one is the portal vein that comes via the small and large intestines, and the other is the hepatic artery that directly arises from the aorta. Normal liver tissue is supplied with blood from both hepatic artery and portal vein, and tumor tissue is supplied with blood from the hepatic artery.

Transcatheter arterial chemoembolization (TACE), which is one of non-invasive techniques that are most frequently carried out for hepatocellular carcinoma (HCC) treatment, is a technique for cutting off arterial blood flow by inserting a catheter into the hepatic artery, injecting Lipiodol, which is an oily contrast medium mixed with an anti-cancer agent, through the catheter, and then inducing embolism. Alternatively, in some cases, an anti-cancer agent may be directly injected into the hepatic artery without the induction of embolism. With the TACE procedure, it is possible to accomplish selective tumor necrosis without great damage to normal liver tissue of a patient. The TACE procedure has a wide application range because it can be applied as long as serious jaundice or ascites does not appear, regardless of the stage of HCC. Up to now, the TACE procedure has been known as a method that contributes to an increase in the survival rate of HCC patients, because it has less limitations in the treatment indications for HCC and is allowed to perform for inoperable HCC patients. However, the procedure has a problem in that the treatment should be carried out several times because a tumor recurs frequently.

Comparison between different phase images of multi-phase (e.g., the pre-contrast images and post-contrast images acquired in the arterial phase, portal phase and equilibrium phase) helical or multi-detector computed tomography (CT) of the liver has been used to detect a residual/recurrent tumor in HCC patients who underwent the TACE procedure as a conventional detection method. For example, by comparing the pre-contrast images with the multi-phase post-contrast images, it is possible to detect a portion, which shows arterial enhancement and delayed wash-out, from a region of interest (ROI) within a Lipiodol-retained HCC as a residual/recurrent tumor portion.

Such a conventional detection method has problems in that it is difficult to perform accurate matching and comparison of a suspicious region between different phases because of a patient's respiration and also it is difficult to diagnose a residual/recurrent tumor in a portion other than the ROI within a Lipiodol-retained HCC.

DETAILED DESCRIPTION OF THE INVENTION

Technical Problem

The present invention is proposed to solve the above conventional problems, and the present invention provides a method and system for initially, accurately, and easily diagnosing cancer using medical imaging acquired in a plurality of energy bands and also differentiate a residual/recurrent tumor from a necrotic tumor after treatment.

Technical Solution

According to the present invention, a system for providing diagnosis-aiding information includes an 'image receiving unit' configured to receive the medical image acquired in the first energy band and the medical image acquired in the second energy band and a 'analysis- and diagnosis-aiding information providing unit' configured to provide diagnosis-aiding information generated by analyzing the medical image acquired in the first energy band and the medical image acquired in the second energy band. The analysis- and diagnosis-aiding information providing unit provides diagnosis-aiding information by measuring the values corresponding to radiation absorption levels, i.e., the Hounsfield unit (HU), in the region of interest (ROI) of the medical image acquired in the first energy band and the medical image acquired in the second energy band and comparing the HU values of the ROI of two medical images.

In an embodiment, an ROI in the medical image acquired in the first energy band and the medical image acquired in the second energy band may be a low tube voltage CT image and a high tube voltage CT image that are acquired through a dual energy CT (DECT) imaging apparatus, and the ratio of the HU values of the ROI between two images may be a ratio of the HU value of the low tube voltage CT image to the HU value of the high tube voltage CT image (i.e., the Low to High Tube Voltage Ratio (LHR)).

In an embodiment, the analysis- and diagnosis-aiding information providing unit may identify at least one of all tissue portions in the liver, including the tumor portions (e.g., the viable tumor portion (VTP), necrotic tumor portion (NTP) and Lipiodol-retaining tumor portion (LTP)) and the normal portions (e.g., the liver portion and blood vessel portion), based on the predetermined LHR values of all tissues. According to the present invention, a method of providing diagnosis-aiding information includes (1) measuring the HU values corresponding to radiation absorption levels of an ROI in the medical image acquired in the first energy band and the medical image acquired in the second energy band, (2) calculating the LHR value from the HU values in the ROIs of two medical images, and (3) providing the diagnosis-aiding information based on the calculated LHR value of the ROIs and the predetermined LHR values of all tissues.

Advantageous Effects of the Invention

As described above, the method and system for providing diagnosis-aiding information using medical imaging according to the present invention may initially, accurately, and easily diagnose cancer and also differentiate a residual/recurrent tumor from a necrotic tumor after treatment.

BEST MODE

Hereinafter, a method and system for providing diagnosis-aiding information by using medical imaging according to the present invention will be described in detail.

Figure 1:
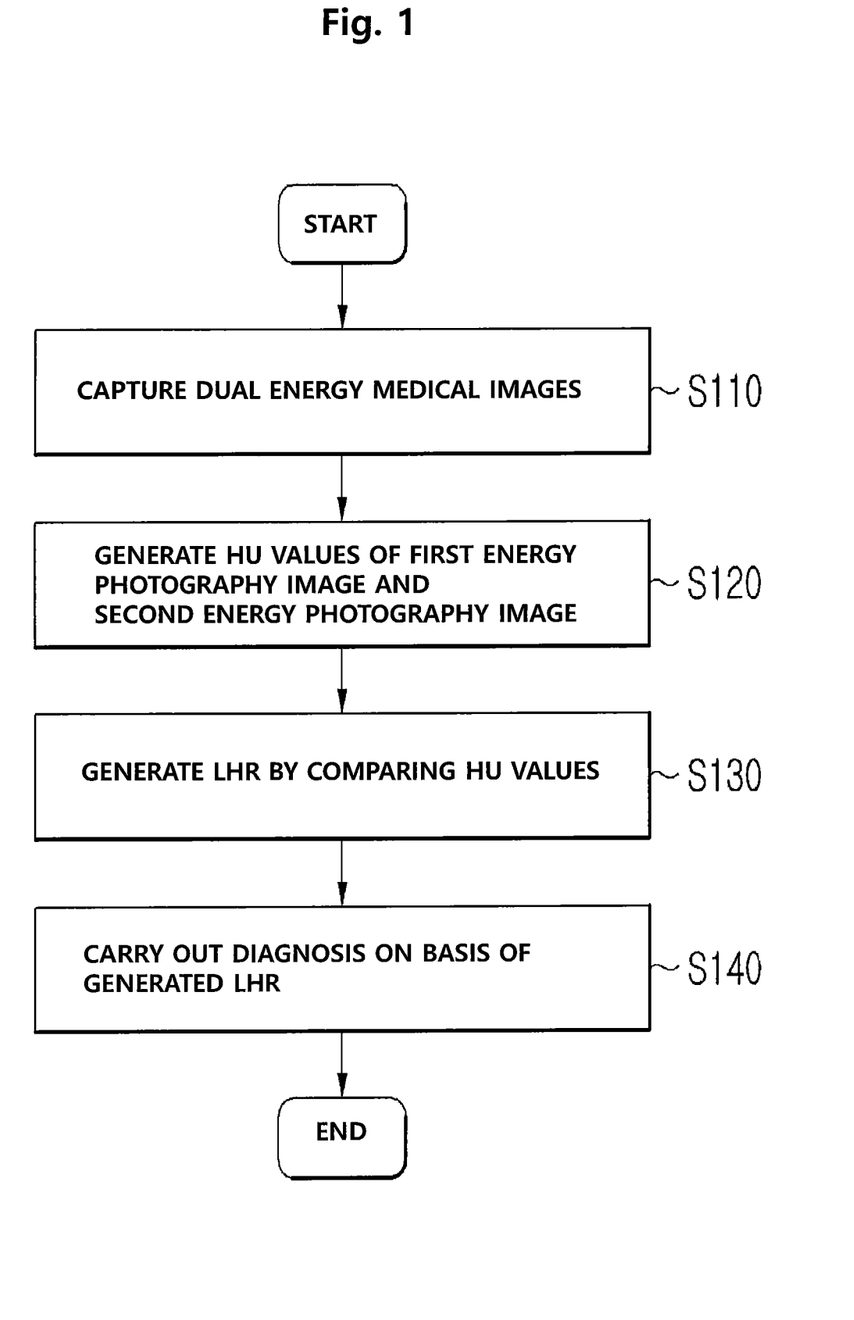
FIG. 1 is a flowchart showing a method providing diagnosis-aiding information in cancer diagnosis according to an embodiment of the present invention.

FIG. 1 is a flowchart showing a method providing diagnosis-aiding information in cancer diagnosis according to an embodiment of the present invention.

Referring to FIG. 1, after a patient is treated with transcatheter arterial chemoembolization (TACE), a computed tomography (CT) image of the liver of the treated patient may be acquired in a medical institution to check follow-up of the treatment.

In the method providing diagnosis-aiding information in cancer diagnosis according to an embodiment of the present invention, a patient undergoes a medical imaging apparatus to acquire medical imaging in a plurality of energy bands, because cancer can be diagnosed using medical imaging acquired in the plurality of energy bands (step S110). For example, according to the present invention, the low tube voltage CT image and the high tube voltage CT image of a patient may be acquired through a dual energy CT (DECT) imaging apparatus and used for providing subsidiary information in cancer diagnosis. For example, the low tube voltage CT image may be acquired in a bandwidth from 75 kVp to 85 kVp, and the high tube voltage CT image may be acquired in a bandwidth from 135 kVp to 145 kVp. The corresponding energy bands are examples, and thus the acquisition of CT images may be performed in other bands.

For convenience of description, the DECT scanner is used as the medical imaging apparatus to acquire medical imaging in a plurality of energy bands. A process of diagnosing cancer using the low tube voltage CT image acquired in a band of 80 kVp and the high tube voltage CT image acquired in a band of 140 kVp will be described below.

When a medical image is acquired, a Hounsfield unit (HU) value is measured from the acquired medical image (step S120). For the DECT, the HU values may be measured from each of the low tube voltage CT image and the high tube voltage CT image. According to an embodiment, the HU value may be measured for each region of interest (ROI) of both low and high tube voltage CT images. For example, the HU value may be measured for each tumor-suspicious ROI of both low and high tube voltage CT images.

The HU represents a radiation absorption level as a relative value. In detail, the HU represents a radiation absorption level of tissue as a relative value according to a criterion in which water is set to be 0 and air is set to be −1000.

When the HU values are measured from the DECT images, a 'Low to High Tube Voltage Ratio (LHR) value is calculated by comparing the HU values in the ROIs of the low tube voltage CT image and the high tube voltage CT image (step S130). The LHR value may be calculated as a ratio of the HU value of the low tube voltage CT image to the HU value of the high tube voltage CT image, as in Equation 1:

$$LHR = \frac{HU \text{ value of low tube voltage } CT \text{ image}}{HU \text{ value of high tube voltage } CT \text{ image}} \quad \text{[Equation 1]}$$

The calculated LHR value may be used to diagnose a cancer (step S140). For example, it is possible to identify and diagnose a viable tumor portion (VTP) in which a residual/recurrent tumor remain after the TACE procedure, a necrotic tumor portion (NTP) in which a tumor is necrotized through the procedure, and a Lipiodol-retaining tumor portion (LTP) in which Lipiodol is retained, by using the calculated LHR value. Also, when the calculated LHR value is used, it is possible to identify the normal tissue portions, for example, the liver, aorta, etc., as well as the tumor tissue portions.

MODE OF THE INVENTION

Figure 2:
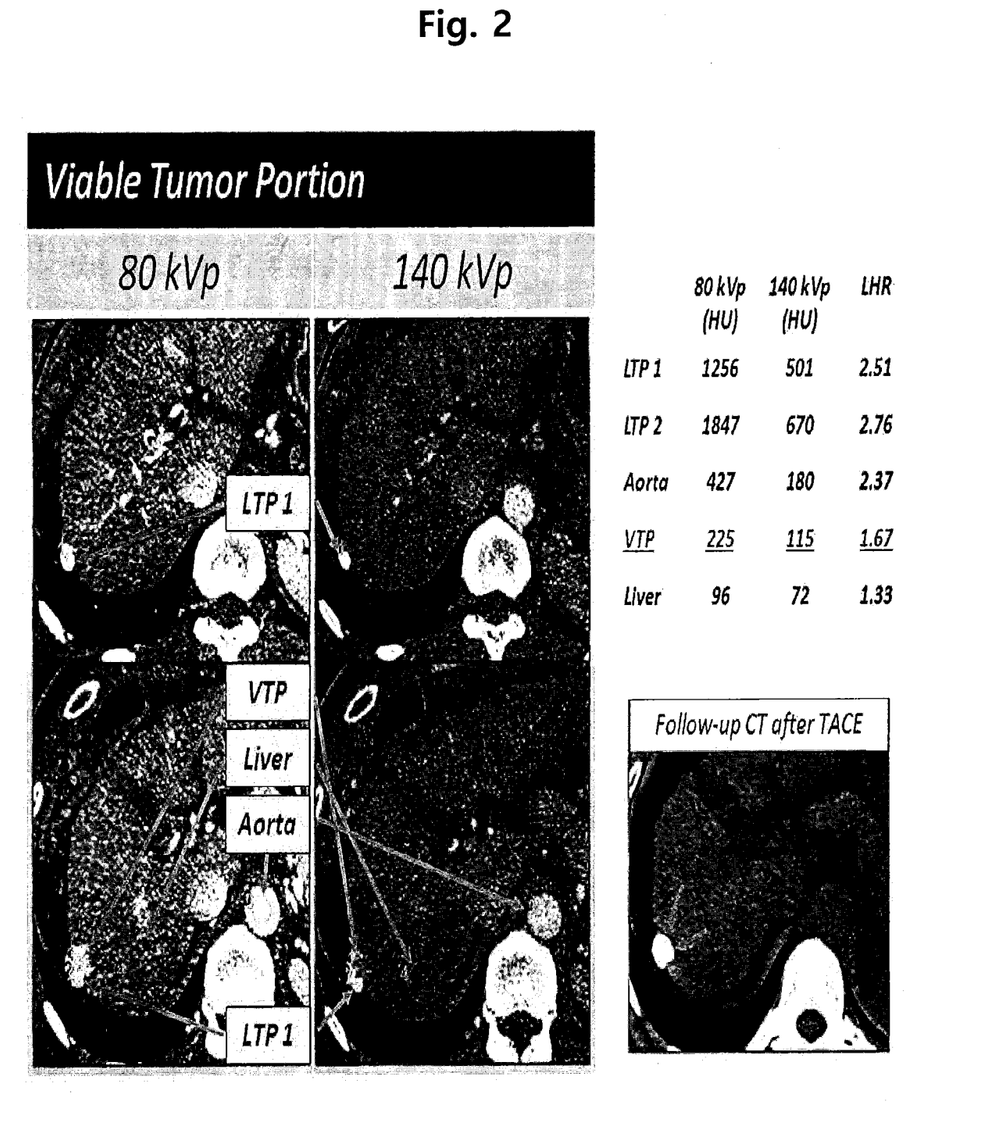
FIG. 2 is a diagram showing a result of calculating an LHR value of a viable tumor portion on the CT image of the liver as a method providing diagnosis-aiding information according to an embodiment of the present invention.
Figure 3:
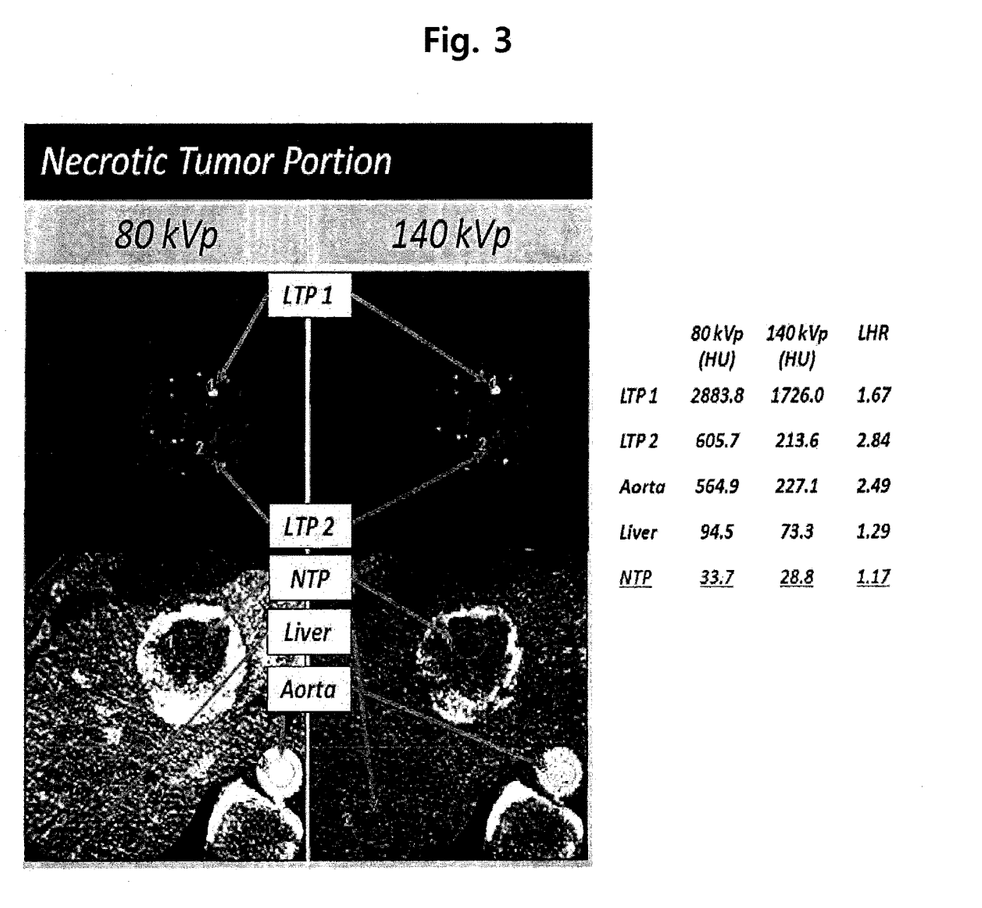
FIG. 3 is a diagram showing a result of calculating an LHR value of a necrotic tumor portion on the CT image of the liver as a method providing diagnosis-aiding information according to an embodiment of the present invention.

FIG. 2 is a diagram showing a result of calculating an LHR of a viable tumor portion (VTP) on the CT image of the liver as a method providing diagnosis-aiding information according to an embodiment of the present invention, and FIG. 3 is a diagram showing a result of calculating an LHR of a necrotic tumor portion (NTP) on the CT image of the liver as a method providing diagnosis-aiding information according to an embodiment of the present invention.

Referring to FIGS. 2 and 3, it can be seen that there is a difference in the LHR values for each portion which is calculated by measuring the HU values of a low tube voltage CT image and a high tube voltage CT image. Then, by comparing the HU values, the LHR value is calculated. For example, it can be seen from FIG. 2 that the LHR value of the VTP is 1.67, which is different from the LHR values (2.51, 2.76) of the LTPs, the LHR value (2.37) of the aorta portion, and the LHR value (1.33) of the liver portion. Similarly, it can be seen from FIG. 3 that the LHR value of the NTP is 1.17, which is different from the LHR values (1.67, 2.84) of the LTPs, the LHR value (2.49) of the aorta portion, and the LHR value (1.29) of the liver portion.

The following verification work was performed to obviously elucidate the usefulness of the above method.

In the verification work, follow-up dual energy CT (DECT) data on 30 hepatocellular carcinoma patients with a history of the TACE procedure, which were acquired beyond the minimum 6-month period to confirm the presence or absence of a recurrent tumor, were used. Also, in order to facilitate the verification, only the arterial phase images of DECT were used in the verification work. However, this method providing diagnosis-aiding information of the present invention may also be applied to images of the phases other than the arterial phase.

The HU values of 19 VTPs, 14 NTPs, 22 LTPs, 30 liver portions, and 30 aorta portions were measured, and the measured values are as described in Table 1.

TABLE 1

| | HU Measurement | |
|---|---|---|
| | 80 kVP | 140 kVP |
| LTP (22) | 2328.35 ± 574.31 | 963.12 ± 405.11 |
| Aorta (30) | 516.65 ± 70.63 | 206.95 ± 24.75 |
| VTP (19) | 199.57 ± 54.93 | 99.07 ± 18.03 |
| Liver (30) | 91.05 ± 17.14 | 70.55 ± 8.77 |
| NTP (14) | 52.22 ± 18.72 | 44.89 ± 0.14 |

Referring to Table 1, it can be seen that the HU values measured for the VTPs used for the verification are distributed within the range of ±54.93 with respect to 199.57 in the low tube voltage CT image and distributed within the range of ±18.03 with respect to 99.07 in the high tube voltage CT image.

Figure 4:
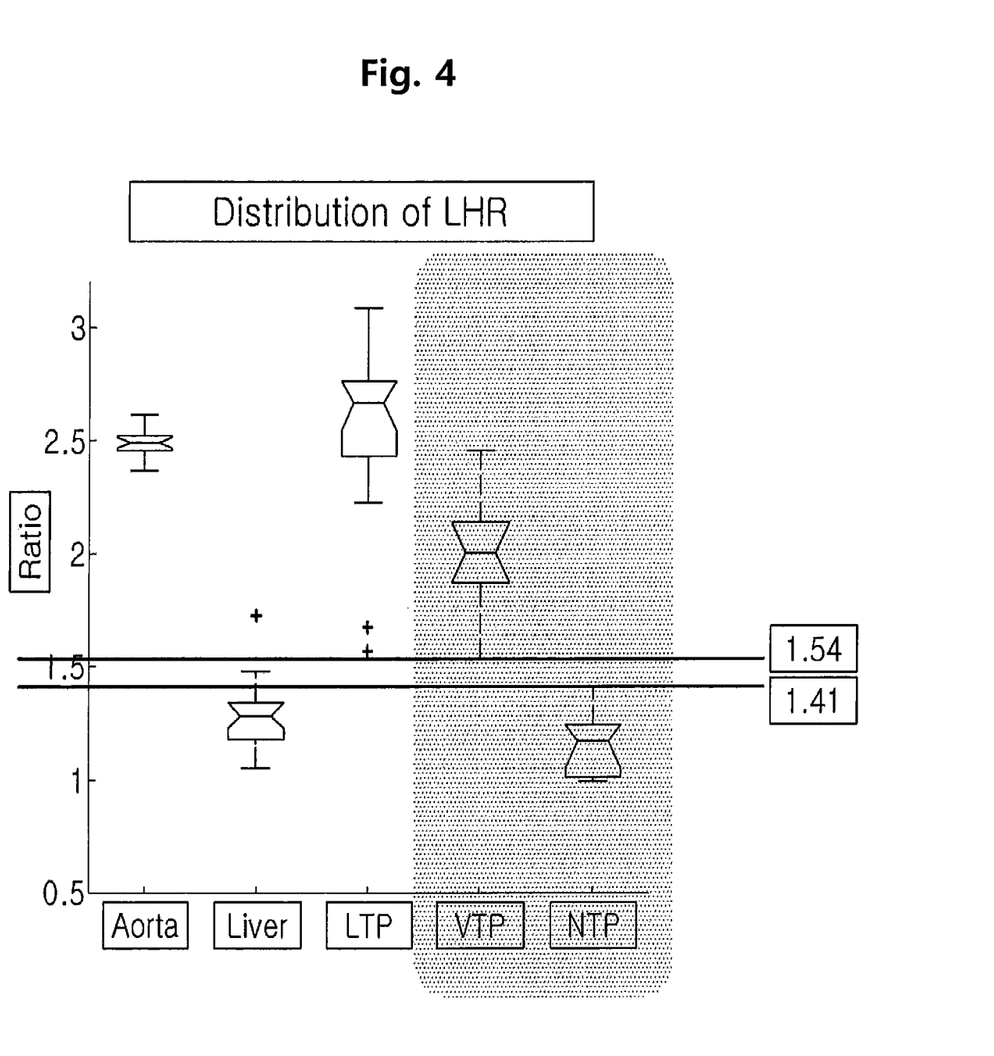
FIG. 4 is a diagram showing distribution of the calculated LHR ranges for each portion.

FIG. 4 is a diagram showing distribution of the calculated LHR ranges for each portion.

It was seen that when an LHR of each portion is calculated on the basis of the HU values of Table 1, the calculated LHR ranges are distributed as shown in FIG. 4. Referring to FIG. 4, it can be seen that the LHR values of the aorta portions are distributed at about 2.5, the LHR values of the liver portions are distributed within the range of 1.2 to 1.4 (at about 1.3), the LHR values of the LTP are distributed within the range of 2.2 to 3.1 (at about 2.7), the LHR values of the VTP are distributed within the range of 1.54 to 2.4 (at about 2.0), and the LHR values of the NTP are distributed within the range of 0.75 to 1.41 (at about 1.2). In a statistical analysis, as shown in FIG. 4, it can be seen that there are statistically meaningful differences between all of the portions except for the aorta portion and the LTP ($P<0.001$).

In particular, the minimal LHR value of the VTP was calculated as 1.54, and the maximal value of the NTP was calculated as 1.41. Accordingly, it can be seen that the VTP and the NTP are definitely distinct and identifiable from each other with respect to the LHR value ranging from 1.41 to 1.54 (at about 1.5).

As seen from the above verification work, it can be seen that each portion may be identified on the basis of the calculated LHR value. According to an embodiment, the tissue type of each portion may also be identified by using the HU value of each portion in addition to the LHR value.

For convenience of description, the description has been made on the basis of the DECT image of patients who underwent the TACE procedure. However, the above method may be applied to any case in which medical images acquired in a plurality of energy bands are used. Also, the above method is applicable to medical images acquired in a plurality of energy bands through a medical imaging apparatus regardless of the presence or absence of the treatment, and may be used to initially diagnose cancer, that is, perform an initial diagnosis of cancer.

When the above method is applied to a computer-aided diagnosis (CAD) system, the CAD system may provide diagnosis-aiding information as a screening method for accurate diagnosis of a residual/recurrent tumor after the TACE procedure.

Figure 5:
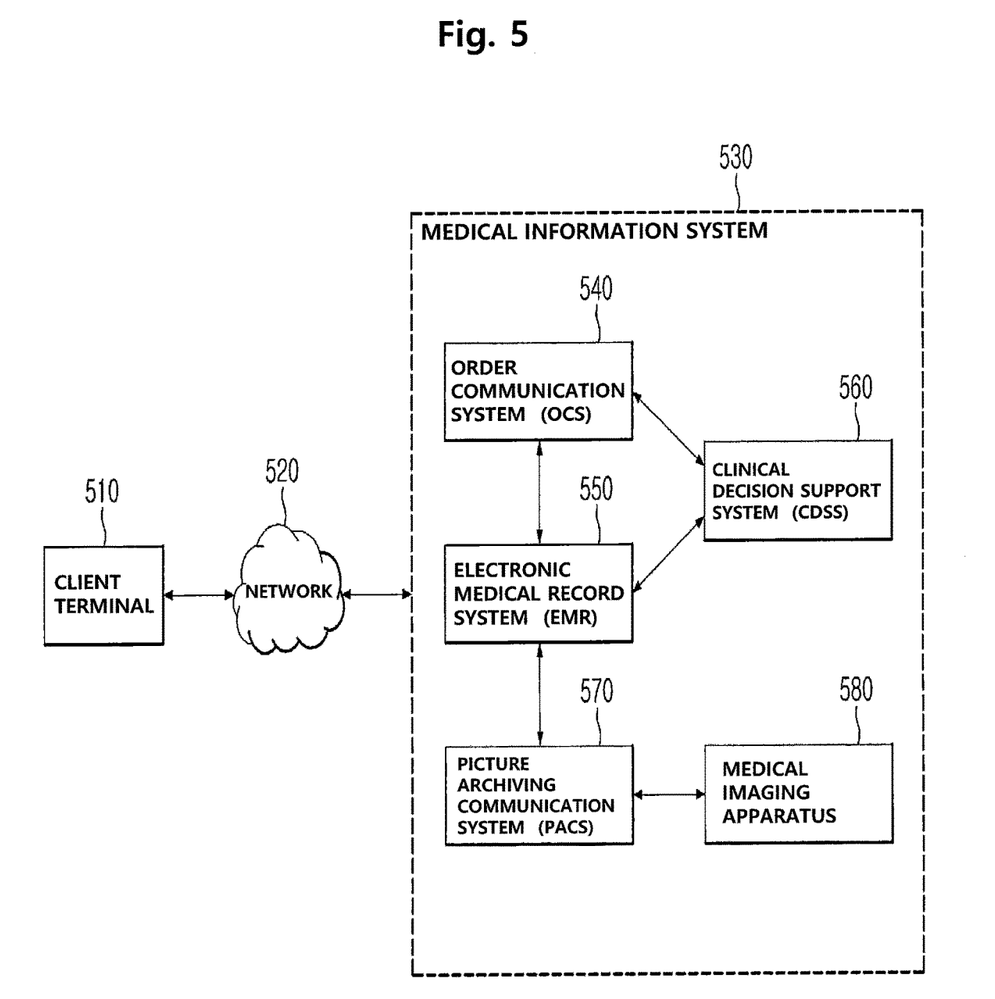
FIG. 5 is a block diagram showing a configuration of a hospital information system according to an embodiment of the present invention.

FIG. 5 is a block diagram showing a configuration of a hospital information system according to an embodiment of the present invention. Referring to FIG. 5, the hospital information system includes a client terminal 510, network 520, and medical information system 530.

The client terminal 510 may access the medical information system 530 under a user's control to request information from the medical information system 530 or transmit information to the medical information system 530. For example, the client terminal 510 may receive the medical information, medical image, diagnosis-aiding information or the like which are provided by the medical information system 530 and may transmit these medical information which are entered by the user. Accordingly, the user may check the medial information, medical image, diagnosis-aiding information or the like stored in the medical information system 530 through the client terminal 510.

The client terminal 510 may include various forms of computing devices. For example, the client terminal 510 includes a mobile terminal such as a tablet PC or smart phone as well as a computer inside or outside a medical institution and a laptop computer.

The medical information system 530 includes an order communication system (OCS) 540, electronic medical record (EMR) system 550, clinical decision support system (CDSS) 560, picture archiving communication system (PACS) 570, and medical imaging apparatus 580.

The order communication system 540 provides the medical information such as a variety of medical information, medical prescriptions or the like to a clinical department over the network 520. The electronic medical record system 550 stores and manages the medical records in the form of data and provides the medical records upon a user's request. The clinical decision support system 560 directly or indirectly provide diagnosis-aiding information needed for a decision-making process for a doctor on the basis of the medical information or medical records stored in the medical information system 530. The clinical decision support system 560 may include a CAD system, etc.

The PACS 570 stores, manages and provides the medical images upon a user's request. Medical images acquired by the medical imaging apparatus 580 or medical images entered through the order communication system 540, electronic medical record system 550, or client terminal 510 may be stored in the PACS 570. The medical imaging apparatus 580 may acquire the medical images of a patient and may include various kinds of imaging apparatus such as a radiation imaging apparatus, a magnetic resonance imaging apparatus, and an ultrasonic imaging apparatus.

A method of operating a hospital information system according to the present invention will be described in detail below.

When a patient is imaged with the medical imaging apparatus 580, which is capable of acquiring medical imaging in a plurality of energy bands, the medical imaging apparatus 580 transmits the acquired medical images to the PACS 570, and the PACS 570 stores the transmitted the medical images. In another embodiment, the PACS 570 may receive the medical images acquired in another medical institution and store the received medical images. For convenience of description, the following description is based on the medical imaging acquired through DECT.

A medical team may interpret the medical images of a patient stored in the PACS 570 and may diagnose the patient. The client terminal 510 may access the medical information system 530 under the medical team's control to inquire about the medical images stored in the PACS 570. For example, the client terminal 510 accesses the electronic medical record system 550 under the medical team's control. When patient identification information to be found is entered from the medical team, the client terminal 510 transmits the patient identification information to the electronic medical record system 550 and receives a medical record of the patient and the medical images stored in the PACS 570.

When a medical team checks the DECT images of a patient stored in the PACS 570 and requests diagnosis-aiding information for the DECT images, the client terminal 510 requests the diagnosis-aiding information for the images from the electronic medical record system 550. In an embodiment, the client terminal 510 may receive a region of interest (ROI) in a medical image from a medical team and request diagnosis-aiding information for the ROI.

For example, cancer is diagnosed through the DECT image of the liver of a patient, the client terminal 510 may request the LHR value of a portion in the medical image under a medical team's control. Alternatively, the client terminal 510 may request diagnosis information for the portions (information for diagnosing at least one of the LTP, VTP, NTP, liver portion, and blood vessel portion) in the medical image according to the medical team's request.

When a diagnosis-aiding information request is received, the electronic medical record system 550 requests diagnosis-aiding information from the CAD system of the clinical decision support system 560. When the diagnosis-aiding information request is received, the CAD system analyzes the corresponding DECT images to generate the diagnosis-aiding information.

Figure 6:
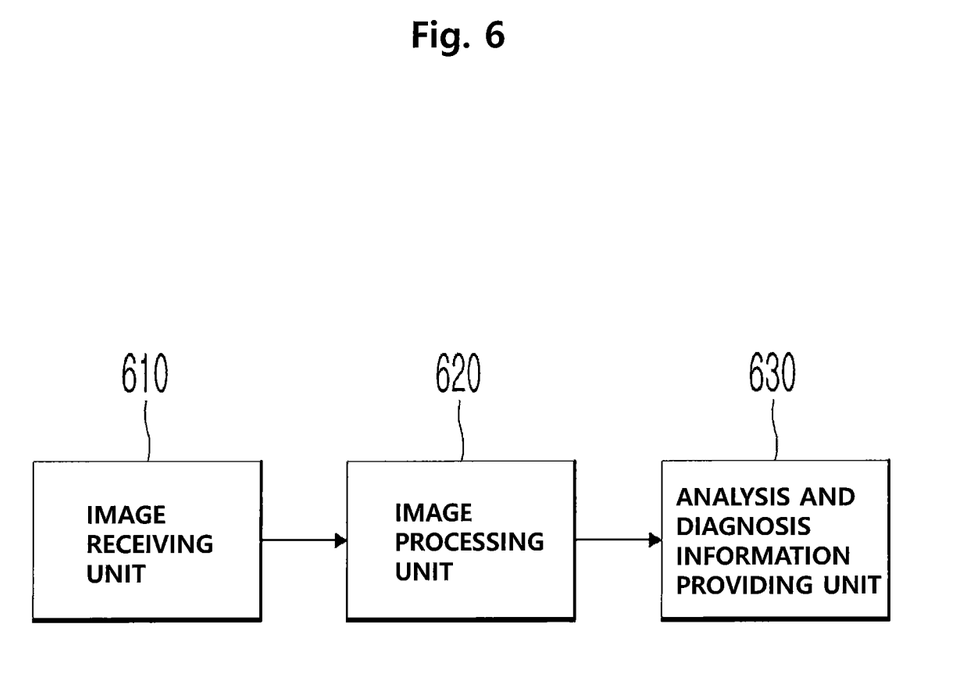
FIG. 6 is a block diagram showing a configuration of a computer-aided diagnosis system according to an embodiment of the present invention.

FIG. 6 is a block diagram showing a configuration of a CAD system according to an embodiment of the present invention. Referring to FIG. 6, the CAD system includes an image receiving unit 610, image processing unit 620, and analysis- and diagnosis-aiding information providing unit 630.

The image receiving unit 610 receives DECT images corresponding to requested diagnosis-aiding information. In an embodiment, the image receiving unit 610 may receive the medical images stored in the PACS 570. When the medical images are received, the image processing unit 620 performs preprocessing on the received images. For example, the image processing unit 620 may determine whether the received images are DECT images and may perform processes such as removal of noise from the images determination of a target area (e.g., an ROI), etc.

The analysis- and diagnosis-aiding information providing unit 630 analyzes the medical images to generate the diagnosis-aiding information. The analysis- and diagnosis-aiding information providing unit 630 measures the HU values of an ROI from the low tube voltage CT image and the high tube voltage CT image, compares the HU values of the ROI, and calculates its LHR value. When the LHR value of an ROI of the medical image is requested as the diagnosis-aiding information, the analysis- and diagnosis-aiding information providing unit 630 provides the LHR value calculated for the ROI. In an embodiment, the analysis- and diagnosis-aiding information providing unit 630 may provide the LHR value together with the HU value for each ROI.

In an embodiment, when diagnosis information of an ROI in the medical image is requested as the diagnosis-aiding information, the analysis- and diagnosis-aiding information providing unit 630 identifies each ROI on the basis of the calculated LHR value of the ROI and the predetermined LHR values of all tissues, and generates diagnosis information. For example, as shown in FIG. 4, the aorta portion is within the predetermined range of about 2.5, the liver portion is within the predetermined range of about 1.3, the LTP is within, the predetermined range of about 2.7, the VTP is within the predetermined range of about 2, and the NTP is within the predetermined range of about 1.2, and the analysis- and diagnosis-aiding information providing unit 630 compares the calculated LHR value of an ROI with the predetermined LHR values of all tissues (e.g., the VTP, NTP, LTP, liver portion and blood vessel portion), identifies to which each ROI corresponds, and provides diagnosis information. In an embodiment, the analysis- and diagnosis-aiding information providing unit 630 may identify each ROI by using additional information other than the LHR values (e.g., the HU values) and provide the diagnosis information.

The CAD system transmits the generated diagnosis-aiding information to the client terminal 510, and the client terminal 510 displays the transmitted diagnosis-aiding information on the screen. A medical team may diagnose a patient using the diagnosis-aiding information displayed on the client terminal 510. For example, a medical team may determine whether the VTP is present by using the LHR value for each ROI that is displayed on the client terminal 510 and may diagnose whether the patient has a residual/recurrent tumor. Alternatively, a medical team may finally check whether the diagnosis (e.g., the VTP, NTP, LTP, liver portion and blood vessel portion) is correct by using diagnosis-aiding information for each ROI that is displayed on the client terminal 510 and may diagnose whether the patient has a residual/recurrent tumor.

Figure 7:
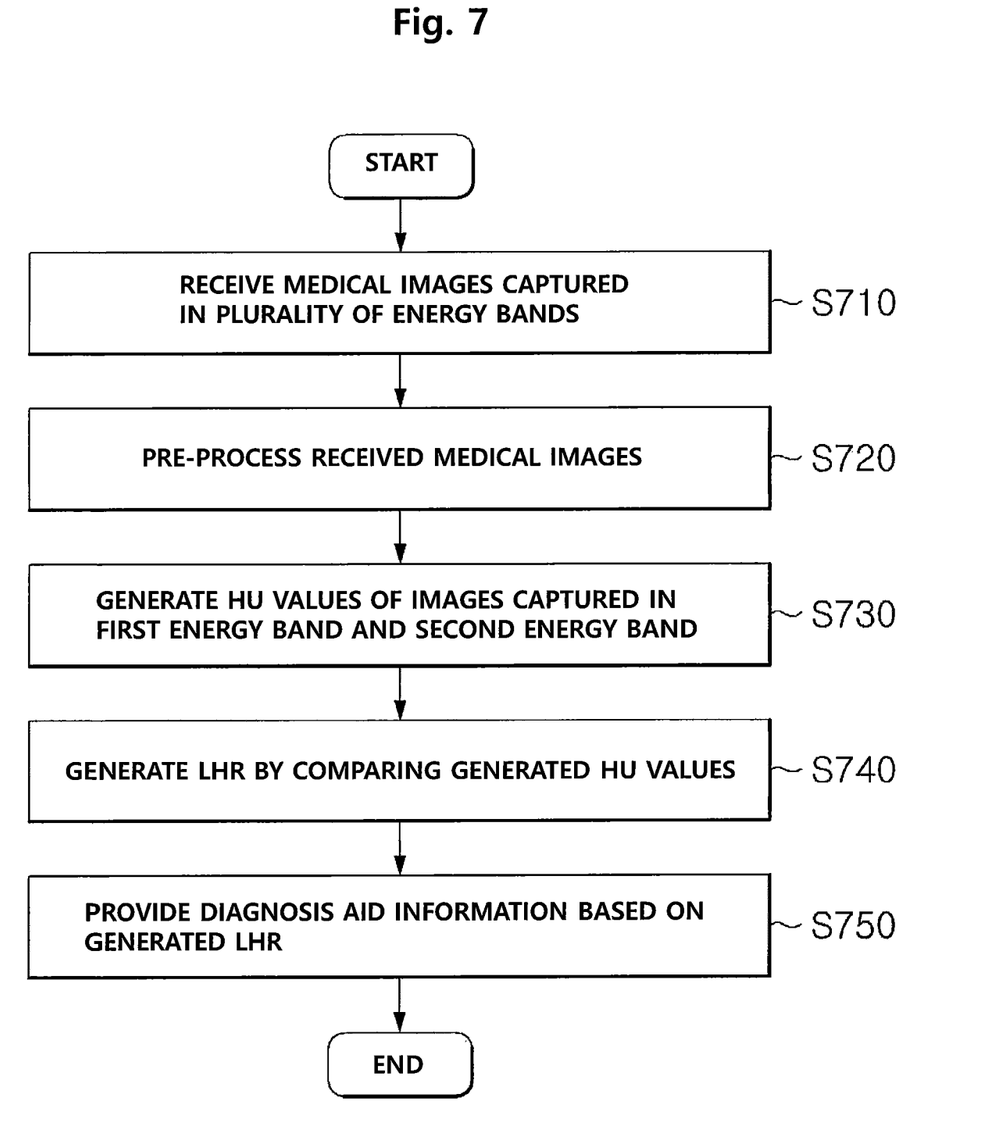
FIG. 7 is a flowchart showing a method of providing diagnosis-aiding information according to an embodiment of the present invention.

FIG. 7 is a flowchart showing a method of providing diagnosis-aiding information according to an embodiment of the present invention.

According to a request of the diagnosis-aiding information, a CAD system receives the medical images acquired in a plurality of energy bands (step S710) and pre-process the received medical images (step S720). In an embodiment, the medical images include the DECT images.

After pre-processing the received medical images, the CAD system generates the HU values of an ROI from the medical image acquired in the first energy band and the medical image acquired in the second energy band (step S730), compares the HU values of the ROI, and calculates the LHR value for the ROI (step S740). For the DECT images, the medical images acquired in the first energy band and the medical images acquired in the second energy band may correspond to the low tube voltage CT image and the high tube voltage CT image, respectively.

When the LHR value is calculated, an analysis- and diagnosis-aiding information providing unit provides diagnosis-aiding information on the basis the calculated LHR value (step S750). For example, when the LHR value in an ROI of the medical image is requested as the diagnosis-aiding information, the analysis- and diagnosis-aiding information providing unit provides the LHR value calculated for the ROI. In another embodiment, when diagnosis information of an ROI of the medical image is requested as the diagnosis-aiding information, the analysis- and diagnosis-aiding information providing unit identifies the ROI on the basis of the calculated LHR value and the predetermined LHR values of all tissues, and provides diagnosis information. For example, the analysis- and diagnosis-aiding information providing unit may identify a status of each ROI on the basis of the calculated LHR value and the predetermined LHR values of all tissues (e.g., the VTP, NTP, LTP, liver portion and blood vessel portion), and provide the status as the diagnosis-aiding information.

The system and method that have been described with reference to FIGS. 5 to 7 may be implemented in the form of a recording medium including instructions executable by a computer such as an application or module executed by the computer.

A computer-readable medium may be any usable medium accessible by a computer and may include volatile and non-volatile media and discrete and integrated media. Also, the computer-readable medium may include both a computer storage medium and a communication medium. The computer storage medium includes the volatile and non-volatile media and the discrete and integrated media, which are implemented in any method or technique for storing information such as a computer readable instruction, data structure, module, or other data. The communication module typically includes the computer readable instruction, data structure, program module, or other data and transmission mechanism of a modulated data signal such as a carrier and further includes any information transmission medium.

A module may mean hardware capable of performing functions and operations according to individual names described in the specification, a computer program code for performing a specific function and operation, or an electronic recording medium (e.g., a processor) equipped with a computer program for performing a specific function and operation.

While the embodiments of the present invention have been described above, the technical idea of the present invention is not limited to the above-described embodiments, and various methods and system for registering medical information may be implemented without departing from the spirit and scope of the present invention.

The invention claimed is:

1. A system for providing diagnosis-aiding information using medical images of a patient, the system comprising:
a computer-implemented image receiving unit configured to receive a first medical image acquired in a first energy band and a second medical image acquired in a second energy band; and
a computer-implemented analysis- and diagnosis-aiding information providing unit configured to provide diagnosis-aiding information generated by analyzing the first medical image acquired in the first energy band and the second medical image acquired in the second energy band,
wherein the computer-implemented analysis- and diagnosis-aiding information providing unit is configured to provide the diagnosis-aiding information by:
measuring first Hounsfield unit (HU) values in a first region of interest (ROI) of the first medical image acquired in the first energy band and measuring second HU values in a second ROI of the second medical image acquired in the second energy band;
calculating an HU value ratio of the first HU values of the first ROI to the second HU values of the second ROI; and
identifying at least one of a viable tumor portion (VTP), necrotic tumor portion (NTP), Lipiodol-retaining tumor portion (LTP), liver portion, and blood vessel portion based on a comparison of the HU value ratio to a predetermined value,
wherein the computer-implemented analysis- and diagnosis-aiding information providing unit is further configured to identify the VTP responsive to the HU value ratio being between 1.54 to 2.4.

2. The system of claim 1, wherein the first and second medical images are acquired through a dual energy computed tomography (DECT) imaging apparatus.

3. The system of claim 2, wherein the first medical image acquired in the first energy band is a low tube voltage computed tomography (CT) image, and the second medical image acquired in the second energy band is a high tube voltage CT image.

4. The system of claim 1, wherein,
the first medical image acquired in the first energy band and the second medical image acquired in the second energy band are a low tube voltage computed tomography (CT) image and a high tube voltage CT image, respectively, and
the HU value ratio is a Low to High Tube Voltage Ratio (LHR).

5. The system of claim 1, wherein the computer-implemented analysis- and diagnosis-aiding information providing unit is further configured to provide the HU value ratio as the diagnosis-aiding information.

6. The system of claim 1, wherein the computer-implemented analysis- and diagnosis-aiding information providing unit is further configured to provide, as the diagnosis-aiding information, a status of the first ROI and the second ROI identified based on the HU value ratio and the predetermined value.

7. The system of claim 1, wherein the computer-implemented analysis- and diagnosis-aiding information providing unit is further configured to identify the NTP responsive to the HU value ratio being between 0.75 to 1.41.

8. The system of claim 1, wherein the computer-implemented analysis- and diagnosis-aiding information providing unit is further configured to identify the LTP responsive to the HU value ratio being between 2.2 to 3.1.

9. The system of claim 1, wherein the computer-implemented analysis- and diagnosis-aiding information providing unit is further configured to differentiate the VTP from the NTP based on the HU value ratio being between 1.41 to 1.54.

10. A method of providing diagnosis-aiding information using medical images of a patient, the method comprising:
measuring first Hounsfield unit (HU) values in a first region of interest (ROI) of a first medical image acquired in a first energy band and measuring second HU values in a second ROI of a second medical image acquired in a second energy band;
calculating an HU value ratio of the first HU values of the first ROI to the second HU values of the second ROI; and
providing the diagnosis-aiding information based on identifying at least one of a viable tumor portion (VTP), necrotic tumor portion (NTP), Lipiodol-retaining tumor portion (LTP), liver portion, and blood vessel portion based on a comparison of the HU value ratio to a predetermined value,
wherein providing the diagnosis-aiding information comprises identifying the VTP responsive to the HU value ratio being between 1.54 to 2.4.

11. The method of claim 10, wherein the first medical image acquired in the first energy band and the second medical image acquired in the second energy band are, respectively, a low tube voltage computed tomography (CT) image and a high tube voltage CT image that are acquired through a dual energy computed tomography (DECT) imaging apparatus.

12. The method of claim 10, wherein the first and second HU values correspond to radiation absorption levels.

13. The method of claim 12, wherein the HU value ratio is a Low to High Tube Voltage Ratio (LHR), and wherein the first medical image is a low tube voltage computed tomography (CT) image and the second medical image is a high tube voltage CT image.

14. The method of claim 10, wherein providing the diagnosis-aiding information further comprises providing the HU value ratio as the diagnosis-aiding information.

15. The method of claim 10, wherein providing the diagnosis-aiding information further comprises providing, as the diagnosis-aiding information, a status of the first ROI and the second ROI identified based on the HU value ratio and the predetermined value.

16. The method of claim 10, wherein providing the diagnosis-aiding information further comprises identifying the NTP responsive to the HU value ratio being between 0.75 to 1.41.

17. The method of claim 10, wherein providing the diagnosis-aiding information further comprises identifying the LTP responsive to the HU value ratio being between 2.2 to 3.1.

18. The method of claim 10, wherein providing the diagnosis-aiding information further comprises differentiating the VTP from the NTP based on the HU value ratio being between 1.41 to 1.54.

* * * * *